United States Patent
Patel et al.

(10) Patent No.: US 8,496,837 B2
(45) Date of Patent: Jul. 30, 2013

(54) REACTOR FOR REDUCTIVE CONVERSION REACTIONS USING PALLADIZED BACTERIAL CELLULOSE

(75) Inventors: Upendra Patel, Mumbai (IN); Sumathi Suresh, Mumbai (IN)

(73) Assignees: Department of Biotechnology, New Delhi (IN); Indian Institute of Technology, West Bengal (IN)

( * ) Notice: Subject to any disclaimer, the term of this patent is extended or adjusted under 35 U.S.C. 154(b) by 523 days.

(21) Appl. No.: 12/594,748

(22) PCT Filed: Apr. 2, 2008

(86) PCT No.: PCT/IN2008/000213
§ 371 (c)(1),
(2), (4) Date: Nov. 20, 2009

(87) PCT Pub. No.: WO2008/122987
PCT Pub. Date: Oct. 16, 2008

(65) Prior Publication Data
US 2010/0126945 A1    May 27, 2010

(30) Foreign Application Priority Data
Apr. 5, 2007   (IN) .......................... 691/MUM/2007

(51) Int. Cl.
*C02F 1/70* (2006.01)
*B01D 35/00* (2006.01)

(52) U.S. Cl.
USPC .......... 210/757; 210/150; 210/205; 210/209; 210/219; 210/220; 210/506; 422/222; 422/225; 435/298.1; 435/299.1; 435/303.3

(58) Field of Classification Search
USPC ................. 210/619, 749, 750, 757, 150, 192, 210/205, 209, 219, 220, 504, 506, 510.1, 210/908, 909, 910; 422/211, 222, 224, 225; 435/289.1, 292.1, 298.1, 298.2, 299.1, 303.1, 435/303.3, 305.2
See application file for complete search history.

(56) References Cited

U.S. PATENT DOCUMENTS

| | | | |
|---|---|---|---|
| 6,071,727 A * | 6/2000 | Bungay et al. | 435/298.2 |
| 6,336,561 B1 * | 1/2002 | Kossik et al. | 210/402 |
| 6,953,604 B2 | 10/2005 | Koslow | |
| 6,986,963 B2 | 1/2006 | Evans et al. | |
| 2006/0286434 A1 | 12/2006 | Evans et al. | |

FOREIGN PATENT DOCUMENTS

| | | |
|---|---|---|
| CA | 1156381 | 11/1983 |
| HU | 9802650 A2 | 1/2002 |
| JP | 55127124 A | 10/1980 |

* cited by examiner

*Primary Examiner* — Lucas Stelling
(74) *Attorney, Agent, or Firm* — The Webb Law Firm

(57) ABSTRACT

A process for affecting reductive conversion reactions in a reactor using the palladized bacterial cellulose immobilized on a support for reductive conversion reactions in a reactor.

13 Claims, 5 Drawing Sheets

REACTOR FOR REDUCTIVE CONVERSION REACTIONS USING PALLADIZED BACTERIAL CELLULOSE

FIELD OF INVENTION

The present invention relates to use of palladized bacterial cellulose for reductive conversion reactions. More particularly it relates to the development, design and operation of the reactor comprising the palladized bacterial cellulose immobilized on a support for remediation of pollutants through these reactions.

BACKGROUND OF INVENTION

Industrial and domestic wastewaters require treatment before release into the surrounding environment. Multiple methods of waste water treatment systems involving abiotic and biotic processes are used for the same. Primary treatment involves physical removal of floating and suspended solids by filtration sedimentation, or floatation. Secondary treatment usually employs biological processes for the removal of dissolved impurities and other chemicals.

Various types of reactors are employed for remediation of potable water and industrial waste water. A reactor is an enclosed device that provides specific conditions for mediating and controlling chemical/biochemical reactions. These systems usually employ chemicals or microorganisms as catalysts to catalyze the reactions. The type of reactors include batch reactors, plug flow reactors, continuous flow reactors, sequential reactors, etc.

Abiotic reactors typically employ chemicals, radiation, high temperatures and pressures etc. for mediating reactions. There is increased potential for production of unwanted by-products, odors and corrosive gases. Also, the equipments and chemicals used may be expensive.

A wide variety of advanced oxidation processes (AOPs) have been reported for the removal of recalcitrant pollutants, namely, chlorophenols that include photocatalysis, photooxidation by hydrogen peroxide ($H_2O_2$/UV) and ozone ($O_3$/UV), Fenton's type reactions, wet oxidation, direct oxidation by ozone, chlorine etc. However advanced oxidation processes are non-selective and attack chlorinated and non-chlorinated compounds with equal potency. Thus for a waste stream containing substantial concentration of biodegradable in addition to not so easily biodegradable chlorinated compounds, AOPs may not be economical. AOPs are especially expensive for small and medium scale industrial units. Abiotic processes such as adsorption on activated carbon or other adsorbents, air stripping, reverse osmosis are also expensive and merely result in phase transfer and not destruction of chlorophenols. Reductive dechlorination by zero-valent metals such as $Mg^o$ or $Fe^o$ is very slow and often incomplete. On the other hand bimetallic systems such as $Fe^o$/palladium or $Mg^o$/palladium can achieve complete dechlorination of recalcitrant pollutants such as chlorophenols, DDT, DDD, DDE. However, advantages of such high reaction rate and efficiency, mild reaction conditions and requirement for minimal follow-up treatment will be defeated if reactor design does not permit reuse and recovery of precious catalysts such as palladium.

Biological reactors employ microorganisms such as bacteria, fungi and algae to mediate transformation or degradation reactions. An important feature of a bioreactor is the ability of microbial cells to divide and reproduce. Very often the contents in the waste water itself serve as food to the microbes. However for industrial wastewaters (such as those discharged from chemical industries) easily biodegradable carbon source such as glucose and nutrients (sources of nitrogen and phosphorus) may need to be added to support growth of microorganisms and generate adequate quantity of biomass.

Bioreactors can be classified as aerobic, anoxic or anaerobic type depending upon the environmental conditions provided. The mode of growth of microorganisms within bioreactors may be attached or suspended. In suspended growth systems, such as activated sludge process (aerobic bioreactor), the contaminated water is treated in an aeration tank where a suspended flocs of microbial population aerobically degrades organic matter and produces $CO_2$, $H_2O$, and new cells. In anaerobic reactors such as upflow anaerobic sludge blanket (UASB) reactor, the bacterial population form granules that settle rapidly in the reactor. In attached growth processes microorganisms are immobilized on the surface of support materials such as plastic, acrylic etc. Bioreactors are widely used for their economical benefits and find extensive applications for treatment of domestic and industrial (such as pharmaceutical) waste waters.

Degradation of chlorinated pollutants by bacteria requires strict anaerobic conditions and very long acclimation (adaptation) period. Typically biological treatment of industrial discharges contaminated with chlorinated pollutants would require several days or weeks in anaerobic reactors. Concentration of the target pollutants and other conditions like pH, presence of salts and other co-pollutants and redox potential influences the efficiency of remediation. Methanogenic and sulfate reducing conditions (redox potential lower than −300 mv) enhances reductive dechlorination but denitrifying conditions inhibits reductive chlorination. A practical difficulty faced under field conditions is to provide favorable redox potential for reductive degradation of chlorinated pollutants. Aerobic degradation of chlorophenols like PCP involves ring cleavage prior to dechlorination and such products may be toxic. For example, the metabolite of aerobic biodegradation of pentachlorophenol, namely tetrachlorohydroquinone is more toxic than pentachlorophenol.

The limitation with bioreactors is the requirement of a growth medium at pH near neutral which contains biodegradable carbon source such as glucose or sucrose and nutrients (nitrogen and phosphate). Toxicity of the pollutants will either kill the bacterial cells or limits their growth (slow growth), and therefore require special design approaches. Low or very high ambient temperatures can significantly decrease biodegradation rates, resulting in increased maintenance time. Efficiency of bioreactors is reduced due to unwanted growth of problematic microorganisms that may preferentially colonize bioreactors. Disposal of resultant biosludge laden with adsorbed pollutants such as chlorinated compounds pose risk of ground water contamination due to leachate generation. Also incineration of the biosludge can lead to formation of toxic chlorinated dioxins. Air pollution controls may be required if there is volatilization of pollutants from bioreactors.

Catalysts

Remediation of potable water and industrial waste waters mainly containing chlorinated pollutants such as DDT, DDD, DDE and pentachlorophenol (PCP) is possible through reductive degradation reactions that are mediated by systems employing palladium (such as magnesium/palladium) as the reducing catalyst. The major hurdle to the field scale application of reductive conversion reactions mediated by systems employing palladium as the reducing catalyst is that the expensive reducing catalyst, namely palladium is either lost with the treated effluent or remains in the reaction system with residual solids in irrecoverable and unusable form. Thus, immobilized palladium which can be recovered and reused is preferred.

There are a number of commercially immobilized palladium catalysts available in the prior art. The choice of support material is extremely important and literature reveals various types of support materials like carbon, alumina, silica, zeolites, chitin, chitosan, amino acids and, metal oxides such as $TiO_2$, MgO, $ZrO_2$. Pd/C and Pd-alumina are some of the commercially available immobilized palladium catalysts. The main disadvantage of the present practice is expense, which precludes the field scale application. In addition there is no information on the application of these catalysts in reactors. Another disadvantage of the present practice is selectivity in action with respect to target pollutants. Also the catalytic activity and stability of immobilized palladium is strongly influenced by the type of support material used. It is also found that HCl is often released as the product of dehalogenation reaction and as a result of which the support materials are degraded and also undergo unwanted ion-exchange reaction with HCl leading to the loss of selectivity and activity of the catalyst. Thus, there is a need to explore alternative eco-friendly support materials for immobilizing palladium and design an indigenous reactor for reductive conversion reactions and for remediation of pollutant wastes.

U.S. Pat. No. 6,986,963 discloses employment of metallized bacterial cellulose in the construction of fuel cells and other electronic devices. The fuel cell includes an electrolytic membrane comprising of membrane support structure comprising of bacterial cellulose, an anode disposed on one side of the electrolytic membrane and a cathode disposed on an opposite side of the electrolytic membrane. The catalyst is disposed in or on the electrode support structure. However, the application of U.S. Pat. No. 6,986,963 is in electrical and electronic device manufacture where in the metallized bacterial cellulose is used as electrode. This application does not teach the use of bacterial cellulose immobilized and palladized in situ for hydrogenation reactions. It also does not teach the design and development of the palladized bacterial cellulose in reactors.

CA Patent No. 1156381 discloses a procedure for purifying wastewater containing chlorinated phenolic compounds. The purification is carried out biologically in a floating bed reactor which has been inoculated with a bacterial population decomposing chlorinated phenolic compounds. Microorganisms have disadvantages associated with their use. Requirement for a growth substrate further increased the costs of the purification. It was also found that toxic conditions affected survival of bacteria and reduced their activity. The present invention does not employ active microorganisms and thus tackles the limitations with biotic reactors.

HU Patent No. 9802650 discloses a bioreactor with cellulose fill. The microbial culture consisted of one or more strains of nitrogen removing bacteria that was established and sustained in the reactor by feed addition. It was found that following the removal of nitrate from water required further treatment with aeration, filtration.

In lieu of the advantages and disadvantages of processes available none of the treatment method posses all the desirable attributes such as high removal efficiency of chloroaromatic and chloroaliphatic pollutants, minimal follow-up treatment, economy, rapid rate of reaction and ease of operation. Clearly, there is a need for the design and development of an indigenous reactor that makes use of a highly efficient non-living catalyst such as palladium immobilized on an ecofriendly matrix for remediation of industrial discharges containing mixture of chlorinated pollutants. A robust, simple to operate and cost effective reactor that can mediate reductive conversion reactions in water containing toxic chlorinated pollutants such as PCP, DDT, DDD, DDE, chloroethylenes, chloroethanes or their mixture is the need of the hour.

The present invention mediates reductive degradation of pentachlorophenol, tetrachlorophenols, trichlorophenols, dichlorophenols and monochlorophenols and their mixture, reductive degradation of aliphatic chlorinated compounds such as chloroethanes and chloroethylenes (trichloroethylene (TCE), perchloroethylene (PCE) which are common contaminants in ground water, reductive degradation of DDT, DDD, DDE to the hydrocarbon end product, diphenylethane.

The present invention may also be applied for reduction of nitroaromatic compounds to amines (anilines). This is important since amine products such as anilines are industrially important intermediates for pharmaceuticals, polymers, herbicides, and other fine chemicals. Currently industries typically use zero valent iron for reduction of nitro groups to amines that is accompanied by the generation of huge quantity iron sludge (insoluble oxides of iron such as FeO, $Fe_2O_3$) that needs to be disposed. For example the rate of generation of iron sludge is ~1.7 ton/ton of H-acid (an important intermediate in the textile dye manufacturing industry) produced. Moreover the iron sludge contains significant concentration of amine mass. The process of reduction involves extensive operations such as separation of iron sludge from product, the washing of iron sludge and dewatering of iron sludge. In case of the reactor (RCCR) developed through this invention this operation is very simple or not required.

In addition, the present invention is also useful in reductive decolorization of specific textile dyes (such as reactive black, drimarene dyes, remazole dyes), food colorants (such as sunset yellow and tartrazine). Currently there is no biological method that can decolorize mixture of dyes that are present in effluents discharged from textile dyeing mills. A specific microorganism can degrade only specific type of dye via the action of enzymes, azoreductases. Chemical oxidation processes such as ozonation and peroxidation are expensive for field scale application. Coagulation and flocculation processes generate chemical sludge which instigates disposal problems.

OBJECT OF INVENTION

The basic object of the present invention is to provide palladized bacterial cellulose which is an eco-friendly and inexpensive support material immobilized on acrylic disc as support for reductive conversion reactions.

Another object of the present invention is to provide a simple procedure for immobilization of bacterial cellulose on to rotating discs in the reactor, and reduction and immobilization of palladium on to bacterial cellulose.

Another object of the present invention is to provide a reactor employing bacterial cellulose impregnated with palladium immobilized on acrylic disc that is alternately exposed through rotation to liquid phase containing dissolved target pollutants and gaseous phase containing hydrogen for facilitating reductive conversion of pollutants.

Yet another object of the present invention is to provide a contact reactor where no precautions are required to exclude oxygen from the reaction phase.

One further object of the present invention is to provide a contact reactor with ability to tolerate adverse reaction conditions such as low pH and resist corrosion by HCl, a by product of hydrodehalogenation of chlorinated pollutants.

One more object of the present invention is to provide a contact reactor with extensive reusability without appreciable loss of catalytic activity of the immobilized palladium.

Further the object is to provide a reactor which provides flexibility of batch as well as continuous flow mode operation.

The other object of the present invention is to provide for an attractive cost effective option for remediation of aqueous phase (potable water or industrial wastewater) contaminated with chlorinated pollutants such as PCP, DDT, chloroethylenes and chloroethanes or their mixture.

A yet another object is to provide a reactor that can be employed for mediating reactions such as conversion of nitro aromatic compounds to amines and reductive decolourization of textile dyes.

SUMMARY OF INVENTION

According to a broad aspect of the invention palladized bacterial cellulose immobilized on a support is provided for reductive conversion of pollutants in a reactor.

According to another aspect of the invention is provided a process or method for effecting reductive conversion reactions in a reactor using the palladized bacterial cellulose.

According to yet another aspect of the invention is provided a rotating catalytic contact reactor comprising acrylic discs rotated using magnetic drive on which bacterial cellulose is immobilized and palladized in-situ.

DETAILED DESCRIPTION OF THE INVENTION

Figure 1:
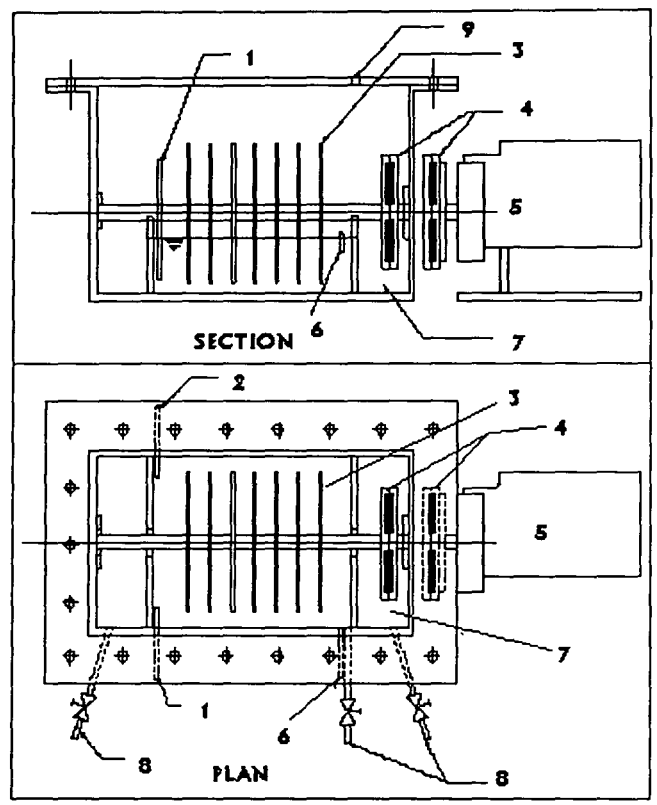
FIG. 1 is a schematic diagram of a rotating catalytic contact reactor according to one embodiment of the present invention.

A biogenic polymer namely bacterial cellulose was explored for its use as a support material for palladium. The major challenges of the invention were: design of a reactor in which bacterial cellulose could be easily immobilized on a support material and thereafter palladized in-situ; the reactor configuration must provide high surface area of palladized bacterial cellulose for hydrogenation reaction; ease of immobilization of the catalyst, palladium on bacterial cellulose; alternate exposure of palladized bacterial cellulose to liquid phase containing the chlorinated pollutant like PCP and gaseous phase containing molecular hydrogen. The third feature is only possible through rotation of the immobilized palladium via liquid and gaseous phase and was essential in view of the reaction mechanism that is involved in reductive degradation such as dechlorination of target pollutants. In the first step of the reaction, the target pollutant from the liquid phase is physically adsorbed onto the surface of the immobilized catalyst, palladium. In the next step, molecular hydrogen from the gaseous phase is dissociatively adsorbed onto palladium thereby generating highly reactive species of hydrogen (nascent hydrogen or palladium hydride) that mediate in-situ (on-site) reductive degradation of adsorbed target pollutants such as PCP, DDT, DDD or DDE. It may be noted that direct transfer of hydrogen from gaseous phase to immobilized palladium is important since the solubility of gas in aqueous phase is very low. A rotating catalytic contact reactor was developed as shown in FIG. 1. This reactor consisted of 7 circular discs of 100 mm diameter providing total surface area of 1100 $cm^2$. Effective volume of the reactor was ~650 mL. The discs were rotated using a magnetic drive to avoid direct connection of motor. This mechanism ensured a leak proof reaction chamber. Bacterial cellulose film was deposited on the surface of circular plates of RCCR by introducing 650 mL of matured coconut water medium which was boiled, cooled and filtered through ordinary filter papers.

Figure 2:
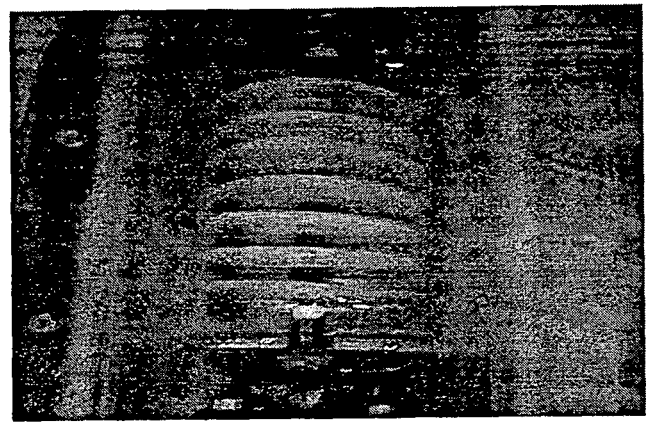
FIGS. 2A and B are a depiction of bacterial cellulose immobilized on serially-arranged acrylic discs.
Figure 2:
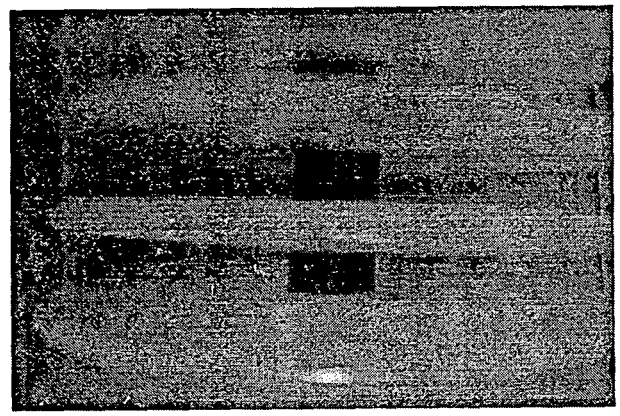
Figure 3:
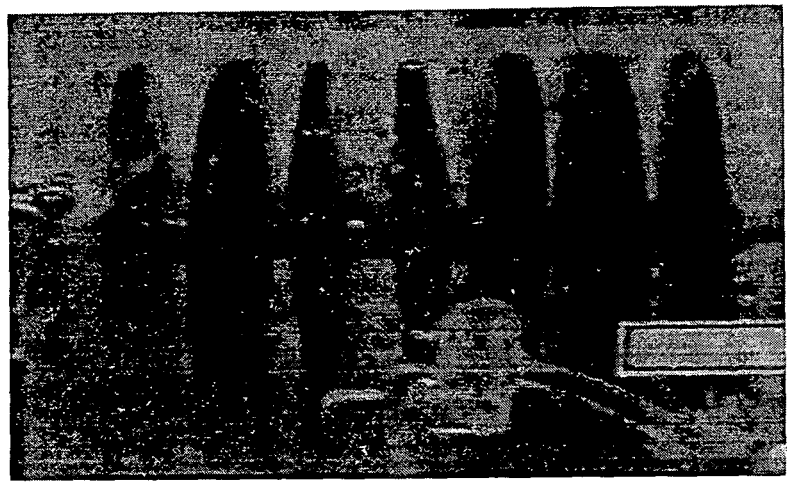
FIGS. 3A and 3B are a depiction of bacterial cellulose immobilized on serially-arranged acrylic discs following palladization.
Figure 3:
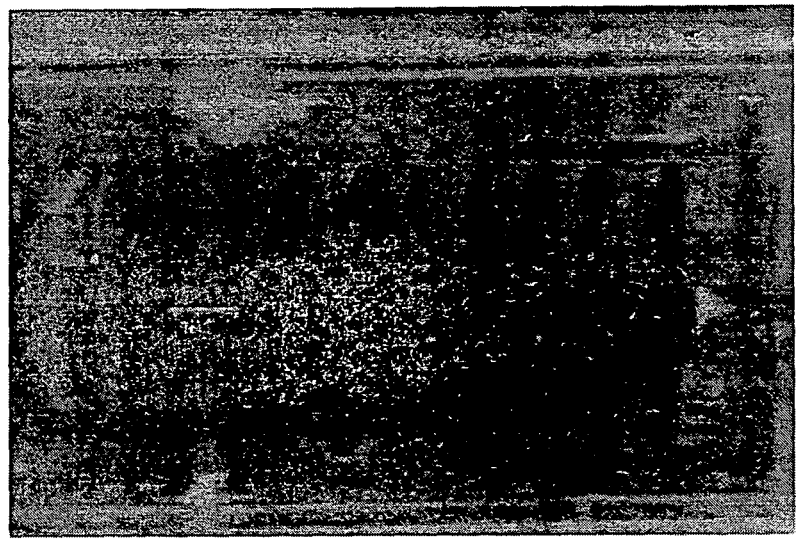

Sucrose, (65 g $L^{-1}$) was dissolved in this coconut water to which 25 g L acetic acid was added. The medium was inoculated with BC producing culture (isolated as per the procedure described in under section 4.1). BC was allowed to deposit on the discs until film thickness of ~2 mm was attained. Pre-treatment and palladization of BC was done. The growth solution was replaced with 1% NaOH and the discs were rotated for 24 h in NaOH solution, following which, the discs were washed thrice by water. Subsequently, 0.5 M sodium acetate (pH adjusted to 4.5 using acetic acid) solution was filled and discs were rotated in it for 2-3 h. Finally the discs were washed with water and incubated in 500 mL of 5 mM solution of $K_2PdCl_6$ prepared in 50 mM sodium acetate solution (pH 4.5) at 70-80° C. The entire set up was maintained until such time (5-6 h) that all the discs turned black in colour due to deposition of metallic palladium. Subsequently the palladized discs were washed in water to wash off the residual $K_2PdCl_6$ solution. FIGS. 2 and 3 show photographs of bacterial cellulose coated discs before and after palladization, respectively.

Isolation of Microbial Culture for Production of Bacterial Cellulose

Culture capable of producing bacterial cellulose was isolated in laboratory as per the tradition followed in Philippines (except that orange residue was used instead of pineapple residue). Three cups of orange residue after extraction of juice, was mixed with 6 cups of water and 1 cup of sugar. The mixture was left undisturbed in a wide mouthed plastic utensil covered by a thin cloth for about a month. Soft, jelly like growth was observed on the sides of the utensil and on top of orange residue after 12-16 days. Once sufficient growth occurred, the jelly like growth was sliced into small pieces and used as the source of cellulose producing bacterial inoculum.

Demonstration of the Reductive Dechlorination of PCP in RCCR

Reactor Operation & Analysis of Products

A distinct feature of RCCR is that the palladized BC (PdBC) discs could be alternately exposed through rotation to liquid phase containing the dissolved target pollutants and gaseous phase containing hydrogen for facilitating reductive degradation. Direct transfer of hydrogen from gaseous phase to immobilized palladium is important since the solubility of gas in aqueous phase is very low.

Dechlorination experiments were conducted in batch and continuous flow mode by introducing water (unbuffered medium) containing 40 mg $L^{-1}$ PCP in the reactor. Hydrogen was continuously bubbled in the reactor. The reactor was maintained at room temperature (26° C.-28° C.) and RPM of 7-8 for all the dechlorination experiments. Rate of PCP dechlorination, formation of the hydrocarbon end product, phenol and release of chloride ions were monitored by analyzing aliquots of the reaction medium at various time points.

DETAILED DESCRIPTION OF ACCOMPANYING FIGURES

FIG. 1 illustrates schematic diagram of rotating catalytic contact reactor (RCCR). The gaseous phase consisting of molecular hydrogen is passed through hydrogen inlet (1). The water containing chlorinated pollutants is introduced in to the reactor through feed inlet (2). The acrylic discs with palladized bacterial cellulose (3) are exposed alternatively to gaseous and aqueous phase by rotation using magnetic drive (4) and variable speed motor (5). There is provided a dry space in the reactor (7). Molecular hydrogen from the gaseous phase gets adsorbed on the palladized surface generating nascent hydrogen which mediates on-site reductive degradation of chlorinated pollutants in the feed. The treated water is let through a outlet (6) and the drains (8) and the vent hole (9) is for outlet of gases as shown in the FIG. 1.

FIGS. 2A and 2B illustrate bacterial cellulose immobilized on serially arranged acrylic discs.

FIGS. 3A and 3B illustrate immobilized bacterial cellulose after palladization. The black color indicates deposition of metallic palladium in bacterial cellulose immobilized on acrylic disc.

Figure 4:
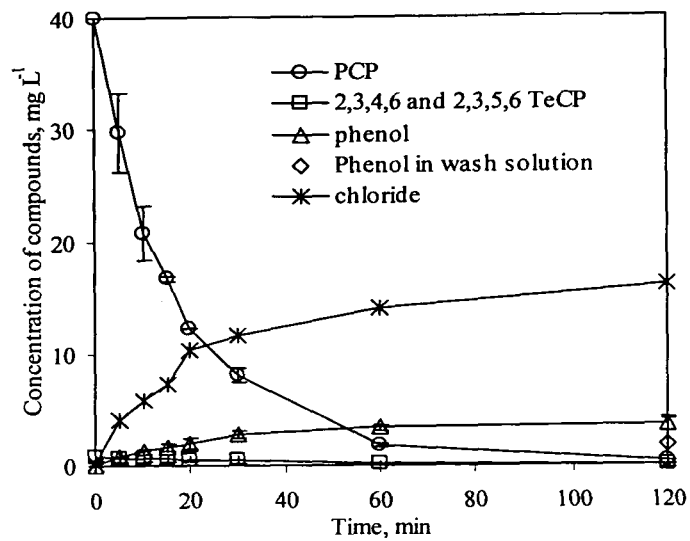
FIGS. 4A and 4B show results of an embodiment of a rotating catalytic contact reactor operated in batch mode including (A) time course of the disappearance of PCP; and (B) a first-order kinetic plot of the disappearance of PCP.
Figure 4:
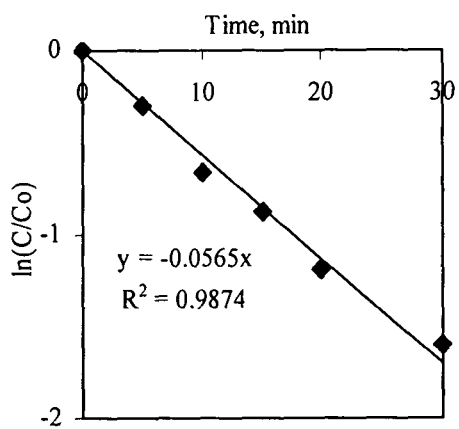

FIGS. 4A and 4B presents performance of the reactor operated in batch mode. The FIG. 4A represents time course profile of PCP disappearance using. RCCR in batch mode along with emergence profiles for free chloride and the hydrocarbon end product, namely phenol. More than 99% of 40 mg L$^{-1}$ of PCP was removed following 2 h of reaction. FIG. 4B represents first order kinetic plot for the same.

The overall reaction is represented below:

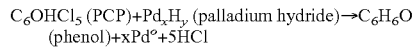

$$C_6OHCl_5 \text{ (PCP)} + Pd_xH_y \text{ (palladium hydride)} \rightarrow C_6H_6O \text{ (phenol)} + xPd^\circ + 5HCl$$

Reaction conditions for batch mode: Liquid volume: 650 mL, initial PCP concentration: 40 mg L$^{-1}$, initial pH: 5.5, RPM: 8, HRT: 2 h, PCP loading: 23.6 µg cm$^{-2}$.

Figure 5:
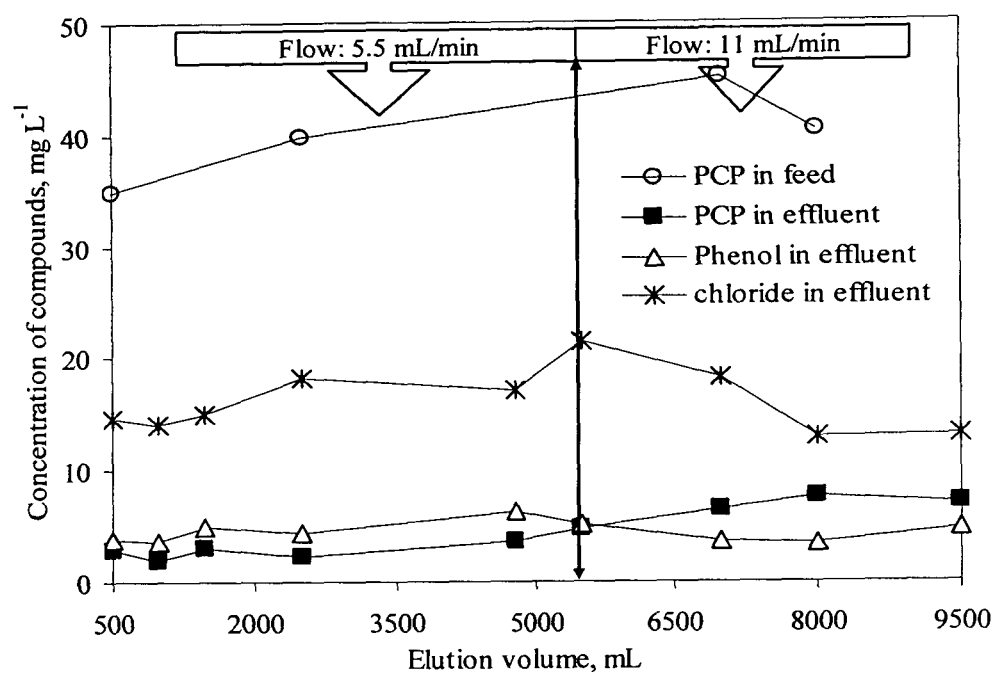
FIG. 5 shows performance of the reactor operated in continuous flow mode.

FIG. 5 represents performance of the reactor operated in continuous flow mode. The graph_presents results related to dechlorination of PCP using the RCR in continuous flow mode. It may be seen that removal of PCP is close to 85-90% through out the study. pH of the effluent was ~5.0. It is interesting to note that while ≧90% PCP removal was achieved in 1 h reaction time in the batch mode, PCP removal in continuous flow mode is ≦90% at HRT values of 1 h and 2 h. Thus efficiency of PCP dechlorination in continuous flow mode is slightly less than that of in batch mode under identical retention times. It may be noted that ~23 L of PCP solution could be treated in batch and continuous flow mode.

Reaction conditions in continuous mode: Liquid volume: 650 mL, initial PCP concentration: 40 mg L$^{-1}$, initial pH: 6.5, RPM: 8, HRT: 1 h and 2 h (flow: 11 mL/min and 5.5 mL/min).

We claim:

1. A rotating catalytic contact reactor comprising:
   a chamber;
   a drive means comprising a variable speed motor and magnetic drive, wherein the variable speed motor is disposed outside the chamber of the reactor;
   a plurality of circular discs inside the chamber of the reactor, wherein the discs are juxtaposed on a rotatable shaft of the drive means;
   a first inlet for passing gaseous phase molecular hydrogen inside the reactor;
   a second inlet for introducing aqueous phase solutions containing dissolved chemical pollutants;
   at least one outlet for allowing exit of aqueous phase solutions;
   at least one drain for the aqueous phase solutions; and
   at least one vent hole for outlet of gases,
   wherein a layer of bacterial cellulose of about 2 mm thickness is disposed on the discs by contacting the discs with coconut water medium and bacterial cellulose-producing culture, and wherein the layer of bacterial cellulose is contacted with salt solution of palladium maintained at between about 70° C. to about 80° C. to dispose metallic palladium on the layer of bacterial cellulose.

2. The reactor as claimed in claim 1, wherein the plurality of discs comprise acrylic discs.

3. A process for reductive conversion reactions comprising:
   providing a rotating catalytic contact reactor comprising a chamber;
   a drive means comprising a variable speed motor and magnetic drive, wherein the variable speed motor is disposed outside the chamber of the reactor;
   a plurality of circular discs inside the chamber of the reactor, wherein the discs are juxtaposed on a rotatable shaft of the drive means;
   a first inlet for passing gaseous phase molecular hydrogen inside the reactor;
   a second inlet for introducing aqueous phase solutions containing dissolved chemical pollutants;
   at least one outlet for allowing exit of aqueous phase solutions;
   at least one drain for the aqueous phase solutions; and
   at least one vent hole for outlet of gases,
   wherein a layer of bacterial cellulose of about 2 mm thickness is disposed on the discs by contacting the discs with coconut water medium and bacterial cellulose-producing culture, wherein the layer of bacterial cellulose is contacted with salt solution of palladium maintained at between about 70° C. to about 80° C. to dispose metallic palladium on the layer of bacterial cellulose;
   feeding untreated aqueous phase waste comprising dissolved pollutants through the second inlet into the reactor continuously or intermittently;
   continuously bubbling molecular hydrogen in gaseous phase into the reactor through the first inlet;
   rotating the discs disposed with palladized bacterial cellulose to alternately contact the aqueous phase waste containing the dissolved pollutants and the gaseous phase containing molecular hydrogen for facilitating in-situ reductive conversion of the pollutants to produce treated aqueous phase; and
   removing the treated aqueous phase from the reactor vessel through the at least one outlet.

4. The process according to claim 3, wherein the untreated waste comprises at least one of dissolved chlorinated compounds, textile dyes, and nitro aromatic compounds.

5. The process according to claim 4, wherein chlorinated compounds of said untreated waste are subjected to reductive dechlorination.

6. The process according to claim 4, wherein textile dyes, are subjected to reductive decolourization.

7. The process according to claim 4, wherein nitro aromatic compounds are subjected to reductive conversion.

8. The process according to claim 4, wherein the textile dyes are selected from the group consisting of reactive black, drimarene dyes, and remazole dyes.

9. The reactor of claim 1, wherein the plurality of discs comprising the layer of bacterial cellulose are rotated in 1% sodium hydroxide solution for 24 h.

10. The reactor of claim 9, wherein the plurality of discs comprising the layer of bacterial cellulose are incubated in 0.5 M sodium acetate solution for 2-3 h.

11. The reactor of claim 10, wherein the plurality of discs comprising the layer of bacterial cellulose are rinsed with water.

12. The reactor of claim 11, wherein the salt solution of palladium is 5 mM $K_2PdCl_6$.

13. A rotating catalytic contact reactor comprising:
a chamber;
a drive means comprising a variable speed motor and magnetic drive, wherein the variable speed motor is disposed outside the chamber of the reactor;
a plurality of circular discs inside the chamber, wherein the discs are juxtaposed on a rotatable shaft of the drive means;
a first inlet for passing gaseous phase molecular hydrogen inside the reactor;
a second inlet for introducing aqueous phase solutions containing dissolved chemical pollutants;
at least one outlet for allowing exit of aqueous phase solutions;
at least one drain for the aqueous phase solutions; and
at least one vent hole for outlet of gases;
wherein the plurality of discs comprise a layer of palladized bacterial cellulose disposed thereon.

* * * * *

UNITED STATES PATENT AND TRADEMARK OFFICE
CERTIFICATE OF CORRECTION

PATENT NO.        : 8,496,837 B2
APPLICATION NO.   : 12/594748
DATED             : July 30, 2013
INVENTOR(S)       : Upendra Patel et al.

Page 1 of 1

It is certified that error appears in the above-identified patent and that said Letters Patent is hereby corrected as shown below:

In the Claims:

Column 8, Line 53, Claim 3, after "reactor" delete "vessel"

Signed and Sealed this
Twenty-eighth Day of January, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,496,837 B2                                     Page 1 of 1
APPLICATION NO.   : 12/594748
DATED             : July 30, 2013
INVENTOR(S)       : Upendra Patel et al.

It is certified that error appears in the above-identified patent and that said Letters Patent is hereby corrected as shown below:

Title Page of the Patent, Column 1, Item (73) Assignees, Line 3, delete "West Bengal" and insert
-- Powai, Mumbai --

Signed and Sealed this
Seventh Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,496,837 B2
APPLICATION NO.   : 12/594748
DATED             : July 30, 2013
INVENTOR(S)       : Patel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 703 days.

Signed and Sealed this
Fifteenth Day of September, 2015

Michelle K. Lee
*Director of the United States Patent and Trademark Office*